(12) United States Patent
Keller

(10) Patent No.: US 8,088,164 B2
(45) Date of Patent: Jan. 3, 2012

(54) CERVICAL INTERVERTEBRAL PROSTHESIS

(75) Inventor: Arnold Keller, Kayhude (DE)

(73) Assignee: Cervitech, Inc., San Diego, CA (US)

( * ) Notice: Subject to any disclaimer, the term of this patent is extended or adjusted under 35 U.S.C. 154(b) by 1021 days.

(21) Appl. No.: 11/125,312

(22) Filed: May 10, 2005

(65) Prior Publication Data

US 2006/0167552 A1 Jul. 27, 2006

(30) Foreign Application Priority Data

Jan. 26, 2005 (EP) .................................. 05001557

(51) Int. Cl.
*A61F 2/44* (2006.01)
(52) U.S. Cl. ................. 623/17.14; 623/17.11; 623/17.15
(58) Field of Classification Search ............... 623/17.11, 623/17.14, 17.15, 17.16, 21.13; 403/135
See application file for complete search history.

(56) References Cited

U.S. PATENT DOCUMENTS

| | | | | |
|---|---|---|---|---|
| 5,258,031 A * | 11/1993 | Salib et al. | ................. | 623/17.15 |
| 5,401,269 A * | 3/1995 | Buttner-Janz et al. | ...... | 623/17.15 |
| 5,425,773 A * | 6/1995 | Boyd et al. | ................. | 623/17.15 |
| 5,683,465 A * | 11/1997 | Shinn et al. | ................. | 623/17.14 |
| 5,755,796 A * | 5/1998 | Ibo et al. | ..................... | 623/17.16 |
| 5,895,428 A | 4/1999 | Berry | | |
| 5,899,941 A * | 5/1999 | Nishijima et al. | ......... | 623/17.15 |
| 5,989,291 A * | 11/1999 | Ralph et al. | ................. | 623/17.15 |
| 6,146,421 A * | 11/2000 | Gordon et al. | ............. | 623/17.15 |
| 6,368,350 B1 * | 4/2002 | Erickson et al. | ........... | 623/17.14 |
| 6,540,785 B1 * | 4/2003 | Gill et al. | .................... | 623/17.14 |
| 6,706,068 B2 * | 3/2004 | Ferree | ........................ | 623/17.11 |
| 6,899,735 B2 * | 5/2005 | Coates et al. | .............. | 623/17.16 |
| 6,986,789 B2 * | 1/2006 | Schultz et al. | ............. | 623/17.15 |
| 2003/0040802 A1 * | 2/2003 | Errico et al. | ................ | 623/17.14 |
| 2003/0074069 A1 * | 4/2003 | Errico et al. | ................ | 623/17.14 |
| 2003/0229394 A1 * | 12/2003 | Ogle et al. | ..................... | 623/2.14 |
| 2003/0233146 A1 * | 12/2003 | Grinberg et al. | ........... | 623/17.14 |
| 2004/0225295 A1 | 11/2004 | Zubok et al. | | |

FOREIGN PATENT DOCUMENTS

| | | |
|---|---|---|
| EP | 1374807 A1 | 1/2004 |
| WO | WO 02/08701 A2 | 11/2002 |
| WO | WO 03/063741 A1 | 8/2003 |
| WO | WO 2004/028415 A1 | 4/2004 |

* cited by examiner

*Primary Examiner* — Thomas C. Barrett
*Assistant Examiner* — Christian Sevilla
(74) *Attorney, Agent, or Firm* — NuVasive, Inc.; Jonathan Spangler; Marjorie Jarvis

(57) ABSTRACT

A cervical intervertebral prosthesis includes two connection plates adapted for connection to adjacent vertebral bodies and a hinge core. The hinge core and one connection plate together form a hinge with a concave hinge surface on the hinge core and with a complementary convex hinge surface on the connection plate. The hinge core bears on the other connection plate via a slide surface which extends substantially parallel to the direction of the connection plate and which permits a relative movement in this direction and is surrounded by an edge limiting this relative movement. The concave hinge surface encloses the convex hinge surface within a solid angle of at least 90°. The part of the concave hinge surface lying within this solid angle lies inside the recess surrounded by the edge. The stability of the prosthesis with respect to laterally incident forces is thereby increased.

19 Claims, 1 Drawing Sheet

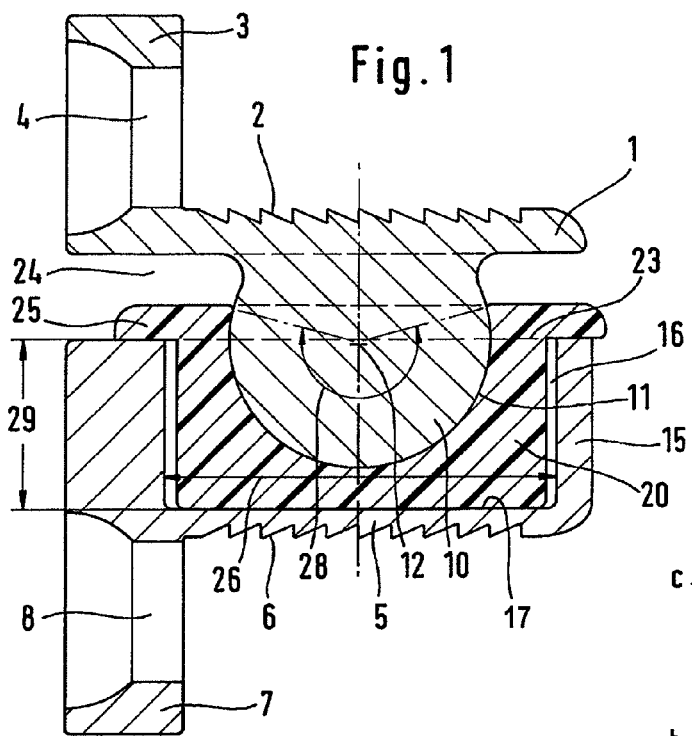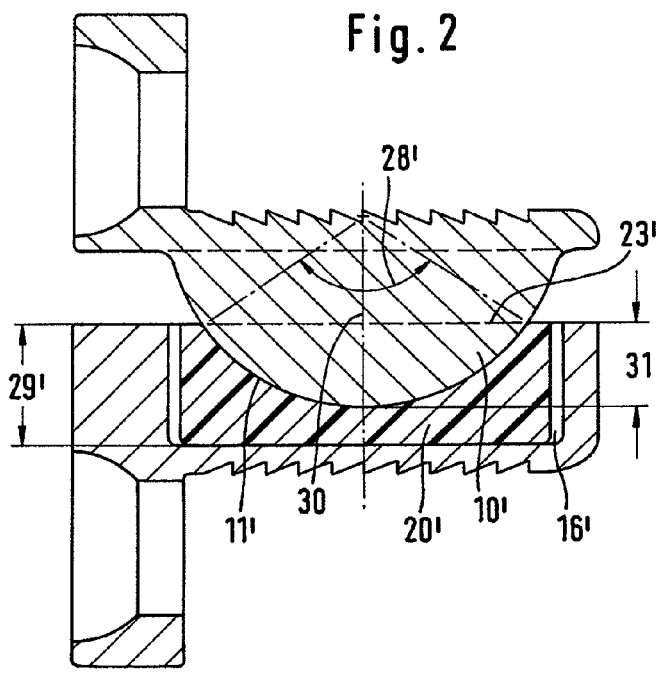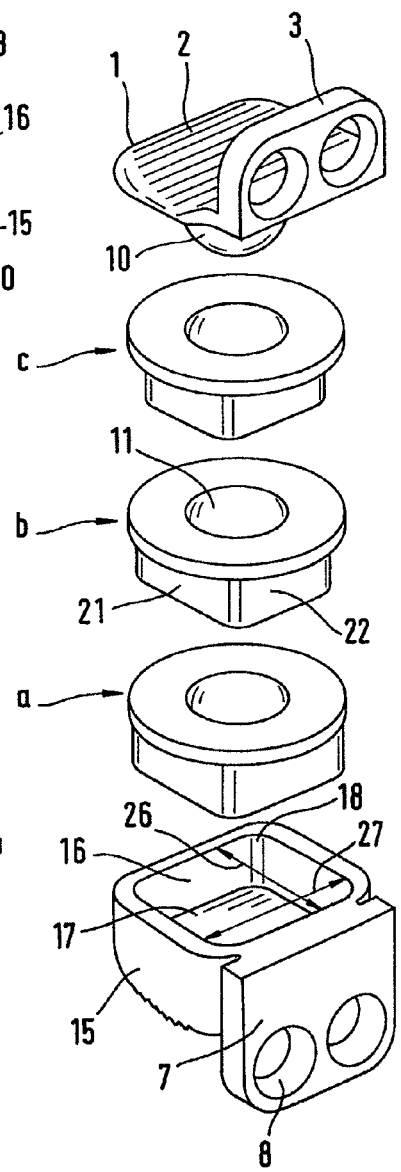

CERVICAL INTERVERTEBRAL PROSTHESIS

FIELD AND BACKGROUND OF THE INVENTION

A cervical intervertebral prosthesis is known (U.S. Pat. No. 6,368,350) which is composed of an upper connection plate and a lower connection plate for connection to the adjacent vertebral bodies, and of a hinge core which, with one connection plate, forms a hinge with a convex hinge surface on the underside of the upper connection plate and with a concave hinge surface on the top side of the hinge core. The hinge core bears on the other connection plate via a slide surface which extends parallel to the direction of extension of the connection plate and which permits a relative translatory movement of the hinge core in this direction with respect to the lower connection plate. This relative movement is limited by means of the slide surface being restricted by a vertical edge. In the known prosthesis, the hinge surface of the hinge core has a very shallow dish-like configuration. This is customary, because it is possible in this way to achieve a low specific surface load. However, this entails the risk that, if the ligaments connecting the relevant vertebral bodies to one another are too weak or stretched, the prosthesis parts may come loose from one another. Although it is known (U.S. Pat. No. 5,895,428) to connect the prosthesis parts to one another by means of a screw passing centrally through the hinge surfaces, this cannot be done in conjunction with the abovementioned translatory freedom of movement of the hinge core parallel to the extension of the connection plates, and, in any case, this is impossible in a cervical prosthesis, because of the confined space.

SUMMARY OF THE INVENTION

It is therefore an object of the invention to make available a prosthesis, of the type mentioned above, which promises sufficient stability even in the case of weak ligaments. The solution lies in the features of the invention, which broadly includes a cervical intervertebral prosthesis including first and second connection plates configured for connection to adjacent vertebral bodies and a hinge core which forms together with the first connection plate a hinge with a concave hinge surface on the hinge core and with a complementary convex hinge surface on the first connection plate. The convex hinge surface bears on the second connection plate via a slide surface which extends substantially parallel to the direction of the second connection plate and which permits relative movement in the direction of the second connection plate. This slide surface is surrounded by an edge limiting the relative movement. The concave hinge surface encloses the convex hinge surface within a solid angle of at least 90°, and the part of the convex hinge surface lying within this solid angle lies inside a recess surrounded by the edge. Other features of the invention are disclosed below.

Accordingly, it is provided that the concave hinge surface encloses the convex hinge surface within a solid angle of at least 90°. This ensures that forces acting obliquely from the side cannot push the convex hinge surface out of the concave hinge surface. Since the stated angle indicates the area within which the concave hinge surface encloses the convex hinge surface, it is referred to below as the enclosure angle. It is expediently at least 110°, more preferably 135°. If, according to a further feature of the invention, it is over 180°, the convex hinge surface is secured completely within the concave hinge surface. The enclosure angle or solid angle is measured as the central angle of a circular cone between radii issuing from opposite points of the edge of the concave hinge surface.

As the stabilization of the prosthesis in the area of the hinge surfaces would be futile if the attachment of the hinge core to the other connection plate was unstable, the invention further provides that the part of the concave hinge surface located within the solid angle of at least 90° lies inside the recess enclosed by the edge. That is to say, this part of the hinge surface lies below the surface spanned by the top face of the edge. The effect is that it is highly unlikely that the hinge core will be able to be pushed, by laterally incident forces, out of the recess of the connection plate in question. If, as has been described above as being advantageous, an enclosure angle of over 90° is chosen, that part of the convex hinge surface extending beyond 90° does not then have to lie in the recess. However, it is advantageous if it does so.

The positioning of the convex hinge surface inside the recess serves not only to secure the hinge core on the connection plate holding it, but also to reduce the overall height of the prosthesis. The radius of the convex hinge surface is so small in relation to the cross section of the hinge core that it lies for the most part inside that part of the hinge core surrounded by the recess of the lower connection plate. The hinge core can be configured such that it lies almost exclusively inside the recess. However, it can be provided with a collar which rests on the top face of the edge of the recess in order to rule out direct contact between the metal parts of the upper and lower connection plates upon flexion of the joint.

The recess should accommodate the hinge core at least to one third, preferably to about half, of its hinge surface radius. A configuration is especially preferred which the recess accommodates the hinge core in substantially to the height of the center point of its hinge surface. The minimum height of the edge surrounding the recess, above the slide surface, should be least one quarter, preferably at least one third, of the antero-posterior (hereinafter "AP") extent of the recess.

Through the interaction of the hinge core with the edge of the recess, the freedom of movement of the hinge core can be predetermined in a desired manner. In an advantageous embodiment, the recess is rectangular, and preferably square, and its boundaries run parallel to the AP direction and transversely thereto. This has the advantage that a recess of the greatest possible dimension can be accommodated in the lower connection plate. In a first variant of this embodiment, a rectangularly delimited hinge core is available which in one direction has a shorter side length than the recess, while its other side length substantially corresponds to the side length of the recess. In this way, depending on the orientation of the hinge core in the recess, the freedom of movement of the hinge core can be restricted to the AP direction (this is the most common scenario) or to the direction perpendicular to the AP direction. If, in a further variant, the translatory movement of the hinge core is to be ruled out entirely, a hinge core is used which is square and has the same dimensions as the recess. If, by contrast, freedom of movement is desired in all directions, the dimensions of the hinge core in all directions are chosen smaller than those of the recess.

BRIEF DESCRIPTION OF THE DRAWINGS

The invention is explained in greater detail below with reference to the drawing, in which:

FIG. 1 shows a sagittal section through a first embodiment,

FIG. 2 shows a sagittal section through a second embodiment, and

FIG. 3 shows an exploded perspective view of two connection plates and, shown between them, different versions of hinge cores.

DETAILED DESCRIPTION OF THE INVENTION

A first connection plate 1 has a surface 2 intended for connection to the cover plate of a first vertebral body. It can be equipped with teeth or other means permitting intimate connection with the bone tissue. A ventral flange 3 includes a screw bore 4 for a bone screw. It will be appreciated that these structural details of the prosthesis will be able to be configured differently. A second cover plate 5 has a surface 6 for connection to the second vertebral body, and a ventral flange 7 with screw bore 8. The first connection plate 1 is depicted at the top, and it is also in most cases used at the top. In the following, therefore, it is designated as the upper connection plate, and the other one is designated as the lower connection plate. The arrangement, however, can also be the other way round.

The underside of the upper connection plate carries a hinge head 10 which forms a convex hinge surface 11 with center point 12. The lower connection plate 5 carries a peripheral edge 15 which surrounds a square recess 16 above a plane slide surface 17. The inner surfaces of the edge 15 extend perpendicularly with respect to the slide surface 17 forming the bottom of the recess 16, and parallel to the AP direction or perpendicularly thereto. The corners 18 are rounded. The dimensions 26, 27 in the AP direction and transversely thereto, respectively, are identical. The connection plates 1, 5 are expediently made of a durable material such as metal.

The hinge core 20, expediently made of polyethylene, ceramic or another material that favors sliding, is located inside the recess 16. It has a plane bottom surface which bears on the slide surface 17 across the greatest possible area and, together with this, forms a sliding bearing for translatory movement. Its side surface 21 extending in the AP direction, and the side surface 22 extending transversely thereto, form a rectangular boundary similar and complementary to the demarcation of the recess 16 by the inner surfaces of the edge 15.

At the upper edge, the hinge core 20 carries a collar 25 which rests on the top face of the edge 15. In the event of a flexion movement, it protects the underside of the upper connection plate 1 from direct contact with parts of the lower connection plate 5. In the lateral areas 24 between the connection plates 1, 5, sufficient space remains for a relative flexion movement.

The hinge core 20 includes a spherical depression which is complementary to the convex hinge surface 11 and forms the associated concave hinge surface. Its center point 12 coincides with that of the convex hinge surface 11. It encloses the convex hinge surface 11 within an enclosure angle 28 of more than 180 degrees. Above the center point 12, it narrows slightly so that the hinge head 10 can escape from it only under elastic deformation and is therefore held securely in it under normal force conditions.

By virtue of the fact that the hinge head 10 is substantially enclosed by the concave hinge surface 11 of the hinge core 20, the flexion joint has a high degree of stability even under the effect of forces acting from the side. Likewise, the hinge core 20 is held with a high degree of stability inside the recess 16 by the edge 15. This is because the hinge core 20 is almost completely surrounded, at any rate to a considerable height, by the edge 15. Its top edge and the surface 23 spanned by the latter are higher than the center point 12 of the concave hinge surface 11. The height 29 of the edge 15 above the slide surface 17 is slightly greater than two fifths of the AP dimension 26 of the recess 16. Even if the hinge core were to be lifted slightly by unanticipated forces, the edge 15 always returns it to the position shown.

The connection plates 1, 5 can be combined with hinge cores of different side lengths. This is illustrated in FIG. 3. The dimensions of the side surfaces of the hinge core "a" are equal (with reasonable play) to the inner surfaces of the edge 15. When it is fitted into the recess 16 of the lower connection plate, it has no translatory mobility relative to the lower connection plate 5. It is therefore used in the case of greatly weakened ligaments, if the prosthesis has to ensure the stabilizing of the intervertebral joint.

The hinge core "c" is smaller than the recess 16 both in the AP direction and transversely thereto. As a result, there is a possibility of limited movement in all directions. This hinge core is used in those cases where the joint can be allowed a translatory movement by a certain distance, but where stabilizing is desired after this distance.

The hinge core "b" represents a cross between the aforementioned possibilities, since the side length of its side surfaces 21 is equal to the side lengths 26, 27 of the recess 16, whereas the pair of side surfaces 22 transverse thereto is shorter. This means that the hinge core "b" is not movable relative to the associated lower connection plate 5 in the direction of the side surfaces 21, but is movable to a limited extent in the direction of the side surfaces 22. This hinge core is used when the need for stabilization differs in different directions. The mobility is in most cases provided in the AP direction, while the connection in the transverse direction is fixed. The reverse option, however, can also be achieved.

FIG. 2 shows an illustrative embodiment which differs from that in FIG. 1 in terms of a more shallow design of the hinge surfaces 11' and a lower hinge core 20'. The enclosure angle 28' is only about 110°. The area of the hinge surface 11' defined by it lies entirely inside the recess 16', i.e. not higher than the upper boundary surface 23'. With its portion 31, the radius 30 of the hinge surface lies more than one third below the boundary surface 23' inside the recess 16'. The height 29' of the recess 16' is equal to about one third of the AP dimension of the recess. The total height of the prosthesis is slightly less than that of the first illustrative embodiment. Nonetheless, it affords a high level of lateral stability.

The invention claimed is:

1. A spinal implant, comprising:
   a first connection plate having a first surface dimensioned to contact a first vertebral body, a second surface opposite the first surface, and a generally spherical hinge extending from the second surface;
   a second connection plate having a first surface dimensioned to contact a second vertebral body, a second surface opposite the first surface, and a walled section extending from the second surface to define a receiving area, wherein the walled section of the receiving area is rectangular;
   a hinge core dimensioned to be received at least partially within the receiving area of the second connection plate, the hinge core including an opening and a generally spherical depression extending from the opening, wherein the opening is dimensioned to be elastically deformed to allow the generally spherical hinge of the first connection plate to pass through the opening and into the generally spherical depression;
   wherein the hinge core slides on a slide surface substantially parallel to the second connection plate after the spinal implant is implanted between the vertebral bodies; and wherein the generally spherical depression encloses the generally spherical hinge within an enclosure angle of more than 180 degrees.

2. The spinal implant of claim 1, wherein at least one of first and second connection plate includes a flange disposed generally perpendicularly to the connection plate with at least one aperture to receive a fixation element to aid in affixing the connection plate to the respective vertebral body.

3. The spinal implant of claim 1, wherein the hinge core includes a base portion and a collar, the base portion positioned within the receiving area of the second connection plate and the collar extending radially outward from the base portion.

4. The spinal implant of claim 1, wherein the hinge core is made of a non-metal material and the connection plates are made of metal.

5. The spinal implant of claim 1, wherein the walled section of the receiving area and the hinge core have substantially the same dimensions.

6. The spinal implant of claim 1, wherein the hinge core lies substantially completely inside the receiving area.

7. The spinal implant of claim 4, wherein the non-metal material is at least one of polyethylene and ceramic.

8. A spinal implant, comprising:
a first connection plate having a first surface dimensioned to contact a first vertebral body, a second surface opposite the first surface, and a generally spherical hinge extending from the second surface;
a second connection plate having a first surface dimensioned to contact a second vertebral body, a second surface opposite the first surface, and a walled section extending from the second surface to define a receiving area, wherein the walled section of the receiving area is square;
a hinge core dimensioned to be received at least partially within the receiving area of the second connection plate, the hinge core including an opening and a generally spherical depression extending from the opening, wherein the opening is dimensioned to be elastically deformed to allow the generally spherical hinge of the first connection plate to pass through the opening and into the generally spherical depression, wherein the hinge core is dimensioned with one pair of sides which has a side length substantially corresponding to a side length of the receiving area, and one pair of sides which has a shorter side length than the side length of the receiving area;
wherein the hinge core slides on a slide surface substantially parallel to the second connection plate after the spinal implant is implanted between the vertebral bodies; and
wherein the generally spherical depression encloses the generally spherical hinge within an enclosure angle of more than 180 degrees.

9. The spinal implant of claim 8, wherein at least one of first and second connection plate includes a flange disposed generally perpendicularly to the connection plate with at least one aperture to receive a fixation element to aid in affixing the connection plate to the respective vertebral body.

10. The spinal implant of claim 8, wherein the hinge core includes a base portion and a collar, the base portion positioned within the receiving area of the second connection plate and the collar extending radially outward from the base portion.

11. The spinal implant of claim 8, wherein the hinge core is made of a non-metal material and the connection plates are made of metal.

12. The spinal implant of claim 8, wherein the hinge core lies substantially completely inside the receiving area.

13. The spinal implant of claim 11, wherein the non-metal material is at least one of polyethylene and ceramic.

14. A spinal implant, comprising:
a first connection plate having a first surface dimensioned to contact a first vertebral body, a second surface opposite the first surface, and a generally spherical hinge extending from the second surface;
a second connection plate having a first surface dimensioned to contact a second vertebral body, a second surface opposite the first surface, and a walled section extending from the second surface to define a receiving area wherein the walled section of the receiving area is square;
a hinge core dimensioned to be received at least partially within the receiving area of the second connection plate, the hinge core including an opening and a generally spherical depression extending from the opening, wherein the opening is dimensioned to be elastically deformed to allow the generally spherical hinge of the first connection plate to pass through the opening and into the generally spherical depression, wherein the hinge core is dimensioned with sides that have a shorter side length than the receiving area;
wherein the hinge core slides on a slide surface substantially parallel to the second connection plate after the spinal implant is implanted between the vertebral bodies; and
wherein the generally spherical depression encloses the generally spherical hinge within an enclosure angle of more than 180 degrees.

15. The spinal implant of claim 14, wherein at least one of first and second connection plate includes a flange disposed generally perpendicularly to the connection plate with at least one aperture to receive a fixation element to aid in affixing the connection plate to the respective vertebral body.

16. The spinal implant of claim 14, wherein the hinge core includes a base portion and a collar, the base portion positioned within the receiving area of the second connection plate and the collar extending radially outward from the base portion.

17. The spinal implant of claim 14, wherein the hinge core is made of a non-metal material and the connection plates are made of metal.

18. The spinal implant of claim 14, wherein the hinge core lies substantially completely inside the receiving area.

19. The spinal implant of claim 17, wherein the non-metal material is at least one of polyethylene and ceramic.

* * * * *